United States Patent
Rowlandson et al.

(10) Patent No.: US 8,326,394 B2
(45) Date of Patent: ***Dec. 4, 2012

(54) SYSTEM AND APPARATUS FOR COLLECTING PHYSIOLOGICAL SIGNALS FROM A PLURALITY OF ELECTRODES

(75) Inventors: Gordon Ian Rowlandson, Milwaukee, WI (US); Joel Quizhen Xue, Germantown, WI (US); Robert Edward Henderson, West Bend, WI (US); Chepur Sudakar Rao, Germantown, WI (US)

(73) Assignee: General Electric Company, Schenectady, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/243,106

(22) Filed: Sep. 23, 2011

(65) Prior Publication Data

US 2012/0010491 A1    Jan. 12, 2012

Related U.S. Application Data

(63) Continuation of application No. 11/763,757, filed on Jun. 15, 2007, now Pat. No. 8,060,175.

(51) Int. Cl.
*A61B 5/04* (2006.01)
(52) U.S. Cl. .............. 600/382; 600/372; 600/509
(58) Field of Classification Search .......... 600/382, 600/372; 439/909, 37, 151
See application file for complete search history.

(56) References Cited

U.S. PATENT DOCUMENTS

| | | |
|---|---|---|
| 4,353,372 A | 10/1982 | Ayer |
| 5,299,572 A | 4/1994 | Chen et al. |
| 5,546,950 A | 8/1996 | Schoeckert et al. |
| 6,115,623 A | 9/2000 | McFee |
| 6,381,482 B1 | 4/2002 | Jayaraman et al. |
| 6,415,169 B1 | 7/2002 | Kornrumpf et al. |
| 6,496,705 B1 | 12/2002 | Ng et al. |
| 6,840,955 B2 | 1/2005 | Ein |
| 7,171,166 B2 | 1/2007 | Ng et al. |
| 7,558,622 B2 | 7/2009 | Tran |
| 2003/0211797 A1 | 11/2003 | Hill et al. |
| 2005/0054941 A1 | 3/2005 | Ting et al. |
| 2007/0073131 A1 | 3/2007 | Ryu et al. |

OTHER PUBLICATIONS

Philips, "Novel solutions to improve detection of sleep disturbance and early indicators of heart failure", Philips Research Technology Backgrounder, website: http://www.research.philips.com/newscenter/archive/2006/carelab/061025-myheart.html. Date accessed: Feb. 26, 2007.
Office Action dated Nov. 3, 2010.
Office Action dated Mar. 24, 2011.
Office Action dated May 12, 2011.

*Primary Examiner* — Lee S Cohen
*Assistant Examiner* — Erin M Cardinal
(74) *Attorney, Agent, or Firm* — Andrus, Sceales, Starke & Sawall, LLP

(57) ABSTRACT

A system and apparatus for obtaining physiological data from a patient. The system and apparatus comprising at least one electrode disposed to collect physiological data from the patient and an electrode connection device having a conductive array formed by a plurality of conductive regions and a plurality of nonconductive regions. The conductive regions are suitable to be connected to the at least one electrode. The electrode may be connected to a first conductive region of the electrode communication device and wherein upon movement by the patient or the conductive array, the electrode is connected to a second conductive region of the conductive array.

20 Claims, 5 Drawing Sheets

SYSTEM AND APPARATUS FOR COLLECTING PHYSIOLOGICAL SIGNALS FROM A PLURALITY OF ELECTRODES

The present application is a continuation of U.S. patent application Ser. No. 11/763,757, filed Jun. 15, 2007, which issued as U.S. Pat. No. 8,060,175 B2 on Nov. 15, 2011.

FIELD OF THE DISCLOSURE

The present disclosure relates to the acquisition of physiological data from a patient. More specifically, the present disclosure relates to the reduction of the number of lead wires that must be attached to the patient to obtain physiological data.

BACKGROUND

Electrocardiography (ECG) is the recordation and analysis of the electrical potential of a patient's heart and is one of the most widely used patient physiological monitoring techniques in healthcare today. In ECG, the electrical potentials of various regions of the heart are monitored through the use of electrodes to obtain data that is indicative of the depolarization and repolarization of the heart muscle tissue. Interpretation of this physiological data can be used to identify many cardiac conditions including, but not limited to, ischemia, myocardial infarction, drug toxicity and arrhythmia. An ECG signal comprises more than the mere collection of biopotentials. Rather, an ECG signal comprises a differential measurement referred to as a lead that measures the voltage across the heart between a reference location and a measurement location. Each of the resulting differential leads are denoted by a reference to the physical location of the electrodes used in obtaining that lead.

In a typical 12-lead ECG measurement, ten electrodes are used to obtain the twelve leads. These electrodes include the standard electrode placements at the right arm (RA), left arm (LA), left leg (LL), and right leg (RL). These standard electrodes are supplemented by the addition of six precordial electrodes that are placed at specific locations around the patient's chest and are denoted by the indications V1, V2, V3, V4, V5 and V6. The standard electrode placement yields measurements of the three standard ECG leads including lead I (LA-RA), lead II (LL-RA), and lead III (LL-LA). The standard electrode placements may also be used to obtain the three augmented ECG leads which are the unidirectional potential vectors starting at the average between two electrodes in the direction of the third electrode. These include aVR, aVL, and aVF.

One problem with obtaining ECG measurements is that typically ten wires corresponding to the ten electrodes attached to the patient must be used in order to obtain the twelve lead ECG as just described. This is a cause of many of the problems associated with obtaining ECG measurements. The large number of wires extending from the patient restricts the patient's movement. A large number of wires may restrict where the patient may place his/her arms and where and how the patient may move about a hospital bed or room. For example, when a patient is sleeping, the wires may restrict the positions in the hospital bed in which the patient may lie, thus leading to an uncomfortable night's sleep and slower recovery.

Alternatively, due to patient movement or clinician movement about the patient, the wires may become tangled. Tangling of the wires may lead to electrode and/or wire damage. Electrode or wire damage may result in inaccurate physiological data recordation leading to reduced clinician ability to diagnose the patient's condition. Furthermore, tangled wires may require additional clinician time in removing, untangling, and replacing the tangled electrodes and lead wires with new connections. Additionally, a large number of wires may result in the wires becoming tangled while they are in storage and as such, a clinician must spend time before the initial application of the wires to the electrodes to untangle the wires. The propensity of the wires to become tangled also increases the chances of damage to the lead wires. In many instances, if a single lead wire becomes damaged or broken, the entire lead wire set must be replaced at additional cost because the lead wires are individually associated with a specific ECG electrode anatomical location.

The problem of tangled and/or damaged wires connected to ECG leads is most prevalent in situations involving the monitoring of active patients and/or the long term monitoring of a patient's ECG characteristics. The more active a patient is the greater the likelihood that wires extending from ECG electrodes may become tangled and/or damaged. Similarly, the longer wires are connected to a patient the greater chance that these wires may become entangled and/or damaged. One example of this situation is in monitoring the patient's ECG overnight. The electrodes and wires are connected to the patient for a long duration of time and the patient may be prone to move in his/her sleep thereby entangling and/or damaging the wires or electrode connections.

Another specific example where the management of wires extending from electrodes is a concern is in body surface potential mapping (BSPM). BSPM provides a more in-depth ECG analysis than a typical 12-lead ECG, as BSPM is typically performed using between 20 and 128 or more electrodes connected to the patient at varying anatomical locations. The purpose behind BSPM is to acquire localized effect information from the heart as opposed to the primarily three dimensional information of the heart taken by a twelve lead ECG. Due to the greater amount of data collected, BSPM is more effective in detecting instances of ischemia and infarction than a twelve lead ECG.

The collection of electrocardiographic data from such a large number of electrodes however, has proved to be burdensome. One method used is to individually attach each electrode and a corresponding lead wire as a scaled up version of a typical twelve lead ECG. If the aforementioned problems exist with respect to ten wires connected to electrodes, than it is obvious that these problems are only magnified as each electrode and lead wire is added to the patient, potentially to more than 128 electrodes and lead wires. Alternatively, a vest or other garment may be utilized that comprises electrodes integrated into the garment that may collect physiological data from the skin of the patient. However, a standardized vest or other garment is limited in that the correct anatomical placement of the electrodes will not be achieved unless the garment is an adequate fit for the patient. Furthermore, the electrode connections with the skin of the patient may be limited as movement between either the patient and/or the garment may pull the electrode away from contact with the skin of the patient. Finally a further limitation of the present BSPM garments is that since it is difficult to manage the exact anatomical placement of the electrodes, it is even more difficult to obtain a twelve lead ECG from the proper anatomical locations to utilize as a reference for the rest of the physiological data collected during the BSPM procedure.

Therefore, it is desirable in the field of collection of physiological data from patients to provide an apparatus and system for limiting the tangling and/or damage to wires extending from the electrodes. It is further desirable in the field to provide an apparatus and/or system that improves the mobility of the patient without tangling or damaging the wires. It is also desirable to have an anatomical reference to the location of the electrodes.

BRIEF DISCLOSURE

Herein disclosed is an apparatus for obtaining physiological data from a patient wherein the apparatus comprises at least one electrode for use as a reference electrode that is suitable to attach to a patient and is suitable to collect physiological data from the patient and a plurality of electrical connection regions forming a conductive array. At least one of the electrodes may comprise a conductive layer configured to transmit the physiological data collected by the electrode, and each of the plurality of conductors being suitable to be connected to the conductive layer. Furthermore, the conductive layer may connect to a first electrical connection region and transmit the collected physiological data to the first electrical connection and upon movement by either the patient or the conductive array, the conductive layer may disconnect from the first electrical connection region and connect to a second electrical connection region.

In an alternative embodiment, an apparatus for obtaining physiological data from a patient is herein disclosed. The apparatus may comprise at least one electrode for use as a reference electrode that is disposed to collect physiological data from the patient and an electrode communication device having a plurality of electrical connection regions forming a conductive array, each of the plurality of conductors being suitable to be connected to at least one electrode. At least one of the electrodes may comprise a first conductive layer suitable for connection to a patient, electrode identifying circuitry that produces a signal indicative of an anatomical location on the patient to which the electrode is to be attached, and a second conductive layer suitable for the transmission of the physiological signal and the signal indicative of an anatomical location.

A system for obtaining physiological data from a patient is also herein disclosed. The system may comprise at least one electrode connected to the patient to collect physiological data from the patient, a data monitor that receives the physiological data collected by the at least one electrode, and an electrode communication device including a conductive array connected to the data monitor and configured for connection to at least one electrode connected to the patient.

DETAILED DISCLOSURE

Figure 1:
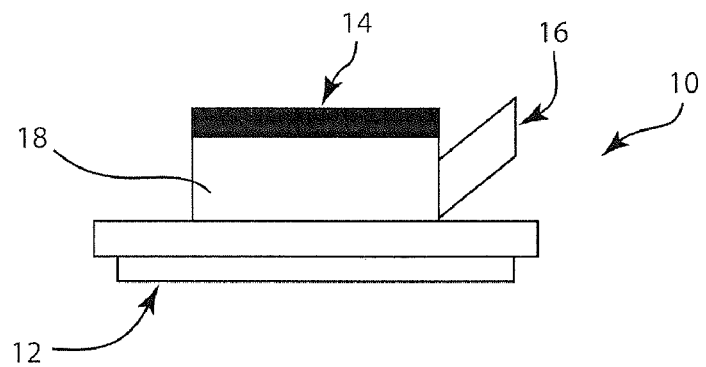
FIG. 1 depicts an embodiment of an electrode.

FIG. 1 depicts an embodiment of a smart electrode 10 that may be used in an embodiment of the system and apparatus as herein disclosed. The smart electrode 10 comprises a first conductive element 12 that is configured for connection to the skin of a patient. The first conductive element 12 may comprise a gel and/or adhesive that both facilitates contact with the skin of the patient and facilitates the collection of physiological data through the skin of the patient. The smart electrode 10 further comprises a second conductive element 14 that is located opposite the first conductive element 12. The second conductive element 14 is configured to transmit any physiological signal collected by the first conductive element 12 when the second conductive element 14 is in contact with another conductive element (not depicted).

The smart electrode 10 may further comprise an external indicia 16. The external indicia 16, while depicted as a tag, may be another type of indication that is affixed or associated with the smart electrode 10. The external indicia 16 may use any of a variety of visual indications such as a symbol, an alphanumeric, a color, or a combination thereof to denote an anatomical location on the patient to which the electrode 10 should be attached. The smart electrode 10 may further comprise electrode identifying circuitry 18. The electrode identifying circuitry 18 produces a signal that identifies the anatomical location on the patient to which the smart electrode 10 is to be attached. The signal produced by the electrode identifying circuitry 18 coincides with the visual indication on the external indicia 16. The identifying signal from the electrode identifying circuitry 18 may be transmitted via the second conductive element 14 to a data monitor (not depicted) along with any physiological signals collected by the first conductive element 12. Therefore, the data monitor may correlate the physiological data collected by the first conductive element 12 with the signal produced by the electrode identifying circuitry 18 that coincides with the anatomical location to which the smart electrode 10 is attached according to the indication of the external indicia 16.

In utilizing the smart electrode 10, the clinician may be in possession of an entire set of smart electrodes 10 each with the external indicia 16 that identifies a specific anatomical location to which the smart electrode 10 is to be attached. The clinician may attach the smart electrodes 10 in any order to the correct anatomical location noted by the external indicia 16. When in communication with a data monitor (not depicted), the first conductive element 12 of the smart electrode 10 collects physiological data from the patient and the electrode identifying circuitry 18 will produce a unique signal that identifies the anatomical location from which the physiological data has been collected.

The electrode identifying circuitry 18 may achieve an indicative signal in a wide variety of circuitry implementations. These implementations may be generally divided into two subsets comprising passive implementations and active implementations based upon the complexity of the operations performed by the electrode identifying circuitry 18. In the passive implementations the electrode identifying circuitry comprises circuitry that uniquely modifies a characteristic of the returned physiological data signal, or uniquely modifies a carrier signal that is sent to each of the electrodes 10 by the data monitor. The passive implementations may modify characteristics such as, but not limited to, the impedance or the phase of one of the signals. A passive implementation may utilize an RL circuit, RC circuit, or another circuit configuration that modifies one or more of the aforementioned signal characteristics or another similar characteristic.

Alternatively, active circuitry implementations for the electrode identifying circuitry 18 actively process the collected physiological data, or a carrier signal injected from the data monitor, to produce an indication of the associated anatomical location of the electrode 10 from which the physiological data is collected. Active implementation embodiments of the electrode identifying circuitry 18 may include the use of an RFD tag that wirelessly transmits a signal back to the data monitor that first identifies when the electrode 10 is being sampled, and further identifies the anatomical location to which the electrode 10 is placed. An alternative embodiment of an active implementation of the electrode identifying circuitry 18 is circuitry that uniquely modulates the collected physiological data or an injected carrier signal, either of which are sent back to the data monitor. The data monitor is then able to translate the unique modulation into an identification of the anatomical location of the electrode 10 including the electrode identifying circuitry 18. A still further embodiment of an active implementation of the electrode identifying circuitry 18 may comprise an analog-to-digital converter (not depicted) that digitizes the collected physiological data for transmission back to the data monitor. The digitized signal may then have additional digital identifying data added to the physiological data as it is transmitted to the data monitor. The data monitor may then interpret the additional identifying digital information resulting in an identification of the anatomical location where the electrode 10 is attached. The examples of active implementations for the electrode identifying circuitry 18 herein presented are intended to be merely exemplarily of active implementation that may be used in the electrode identifying circuitry 18 and are not intended to be limiting on the scope of the implementations of the electrode identifying circuitry 18.

Passive implementations and active implementations herein described may result in the transmission of the collected physiological data and the signal indicative of the anatomical location to the data monitor via a wired data connection. This data connection may comprise a single conductor, or multiple conductors. Alternatively, embodiments of the electrode identifying circuitry 18 including active implementations of the electrode identifying circuitry 18 may transmit either or both of the collected physiological data and the signal indicative of the anatomical location back to the data monitor using the wireless transmission of data. This wireless transmission of data may be a wireless transmission of analog or digital data.

Figure 2:
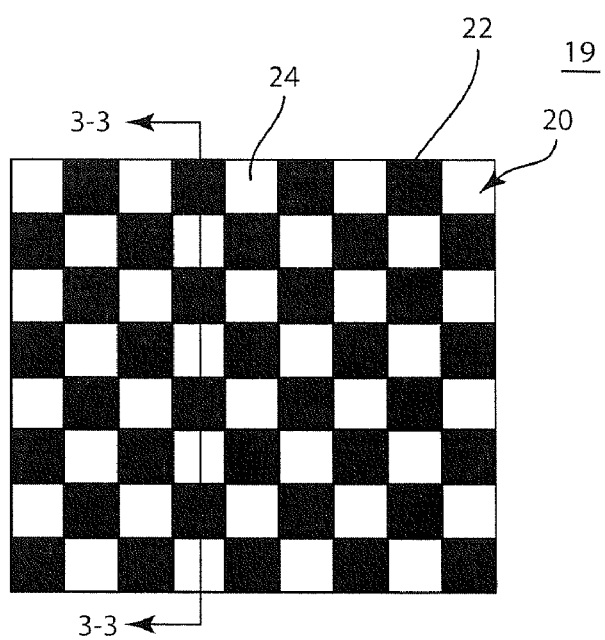
FIG. 2 depicts an embodiment of a conductive array.

FIG. 2 depicts an embodiment of an electrode communication device 19 having a conductive array 20 that may be utilized in the system or apparatus disclosed herein. The conductive array 20 comprises at least one electrical connection region 22 and at least one non-conductive region 24. In a further embodiment, the conductive array 20 comprises a plurality of electrical connection regions 22 and a plurality of non-conductive regions 24. In a still further embodiment, the conductive array 20 is arranged to comprise a plurality of electrical connection regions 22 and non-conductive regions 24 in a checked pattern such as to form an electronic gingham. In still further embodiments of the conductive array 20 the electrical connection regions 22 are each suitable for connection to the second conductive element 14 (depicted in FIG. 1). The electrical connection regions 22 of the electrode communication device 19 facilitate the transfer of both the physiological data and the signal indicative of an anatomical location from the smart electrode 10 depicted in FIG. 1 to a data monitor (not depicted). In a still further embodiment, the non-conductive regions 24 are defined by the electrical connection regions 22 such that the nonconductive regions 24 are gaps or spaces between each of the plurality of electrical connection regions 22. The nonconductive regions 24 may serve to define the electrical connection regions 22 or to insulate the electrical connection regions 22 from each other such that each region 22 is able to independently receive data from an electrode.

In further embodiments of the conductive array 20, each electrical connection region 22 may be smaller than the second conductive element 14 of the electrode 10 as depicted in FIG. 1. Additionally, the area of the conductive array 20 comprised by the electrical connection regions 22 may be greater than the area of the conductive array 20 comprised by the nonconductive regions 24. As such, the second conductive element 14 of an electrode 10 (as depicted in FIG. 1) will always be in contact with at least one electrical connection region 22 since the second conductive element 14 is larger than any of the nonconductive regions 24.

Figure 3A:
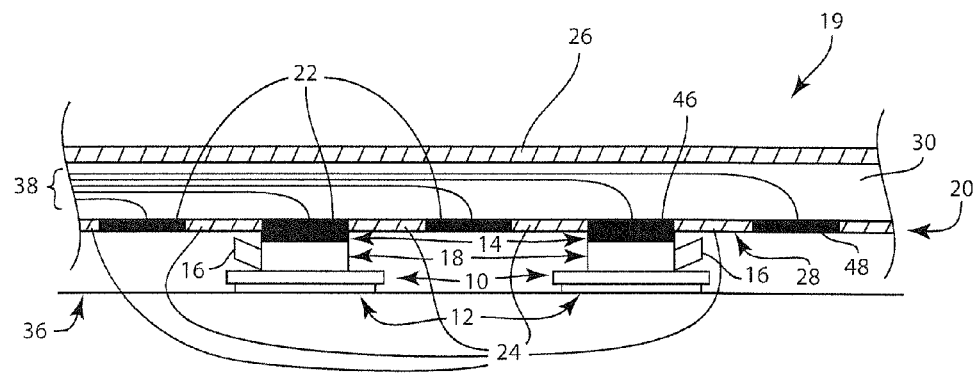
FIG. 3a depicts an implementation of the electrode and the conductive array.

FIG. 3a depicts an embodiment of the electrode communication device 19 as taken along section line 3-3 of FIG. 2. The conductive array 20 comprises a first insulative layer 26 that is disposed to one side of the conductive array 20. The first insulative layer 26 may comprise any material that is suitable for isolating an electrical component from interference due to exterior electronic or electromagnetic sources. The electrode communication device 19 further comprises a second insulative layer 28 that is on the opposite side of the electrode communication device 19 from the first insulative layer 26. In the embodiment shown, the second insulative layer 28 is disposed between the electrical connection regions 22 such that the second insulative layer 28 forms or fills in, the non-conductive regions 24. The second insulative layer 28 may be made of a material that is suitable for providing electronic and electromagnetic isolation to each of the electrical connection regions 22. Furthermore, the second insulative layer 28 may be made of a material that is suitable for contact with the second conductive elements 14 of the electrodes 10 and the patient's skin 36.

The first insulative layer 26 and the second insulative layer 28 define a recess 30 between the first insulative layer 26 and the second insulative layer 28. The recess 30 may be an open space between the two insulative layers, or alternatively, the recess 30 may be filled with another material such as an alternative insulative material (not depicted). A plurality of data wires 38 are shown located within the recess 30. In the embodiment shown, one of the data wires of the plurality of data wires 38 connects to a single electrical connection region 22. The plurality of data wires 38 that are connected to the electrical connection regions 22 run within the recess 30 to a single point where the plurality of data wires 38 meet to form an amalgamated data wire (not depicted) that extends from the electrode communication device 19. In the embodiment herein previously described, the data monitor may associate each of the data wires with a specific electrical connection region 22 and individually monitor the signals collected from each specific electrical connection region 22.

In an alternative embodiment utilizing the heretofore described smart electrode 10 and the electrode communication device 19, the clinician may attach at least one smart electrode 10 to the skin of the patient 36. The clinician may view an external indicia 16 that provides an indication of the anatomical location to which the smart electrode 10 is to be attached. The clinician attaches the smart electrode 10 to the specific location as identified by the external indicia 16. The clinician repeats this until all of the smart electrodes 10 have been attached. The first conductive element 12 creates the interface between the smart electrode 10 and the patient's skin 36 such that the smart electrode 10 is able to collect physiological data from the skin of the patient as well as releasably adhere to the patient's skin 36. The clinician may attach the smart electrodes 10 in any order and may randomly place the smart electrodes 10 at the anatomical location identified by the external indicia 16 as the clinician randomly acquires each of the smart electrodes 10 from where the smart electrodes 10 are stored.

After the smart electrodes 10 have been placed on the patient's skin 36, the clinician places the electrode communication device 19 over the smart electrodes 10. When the electrode communication device 19 is placed over the electrodes 10, the electrical connection regions 22 of the conductive array 20 that contact the second conductive elements 14 of the smart electrodes 10 will receive the physiological data collected by the electrodes 10 and the signals indicative of the anatomical location of the electrodes 10 generated by the electrode identifying circuitry 18. The data and signal received by the connection regions 22 are transmitted via the plurality of data wires 38 back to the data monitor (not depicted). As can be understood in FIGS. 3a and 3b, the second conductive elements 14 may not perfectly align with any one of the electrical connection regions 22. In some embodiments, the second conductive elements 14 may contact more than one electrical connection region 22. In these instances, the data and signals from the smart electrodes 10 may be transmitted back to the data monitor through multiple electrical connection regions 22 and data wires 38. The data monitor may then process the received physiological data and signals indicative of anatomical locations and identify the data and signals received by each of the electrical connection regions 22. In a still further embodiment the data monitor determines the electrical connection region 22 comprising the best or the optimal connection with each second conductive element 14.

Figure 3B:
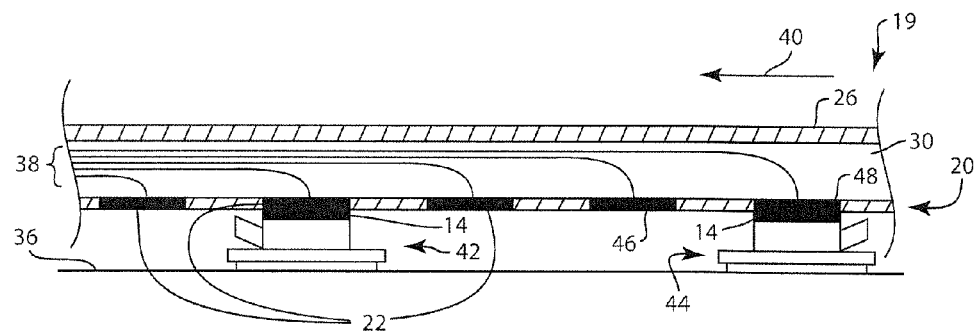
FIG. 3b depicts an alternative embodiment of an implementation of the electrode and the conductive array.

FIG. 3b depicts the electrode communication device 19 after the electrode communication device 19 has been moved in the direction of arrow 40, such as by movement of the patient. Alternatively, arrow 40 may also represent movement that increases the distance between a first electrode 42 and a second electrode 44, such as due to the anatomical locations to which the electrodes 42 and 44 are attached on the patient's skin 36. For instance, the electrodes 42 and 44 may be placed on the chest of the patient and therefore are subject to the expansion and compression of the chest wall during the patient's rhythmic breathing cycle. The expansion of the patient's chest wall would stretch the skin 36 and thereby increase the distance between the electrodes 42 and 44 that are attached to the skin 36 of the patient.

Since the second conductive elements 14 of each of the electrodes 42 and 44 are only in contact with the electrical connection regions 22 and are not fixed thereto, the movement of the entire conductive array 20 or the skin of the patient 36 may cause the second conductive element 14 of the second electrodes 44 to leave contact with the electrical connection region 46 to which it was previously in contact (see FIG. 3a) and to contact one or more alternative electrical connection regions 48. Therefore, even as the patient and/or the electrode communication device 19 moves, the physiological data and the signals indicative of anatomical locations are still able to be transmitted to the data monitor because the electrodes 42, 44 are able to contact any one of the plurality of electrical connection regions 22 and transmit this data. Alternatively, as depicted in FIG. 3b, upon movement by the conductive array 20, the patient's skin 36, or the electrodes 42, 44, not every electrode 42 need to detach from the electrical connection region 22 to which it is connected, but rather some of the connections between the electrode 42 and the electrical connection regions 22 may continue until the electrode 42 or the electrode communication device 19 are moved such that a connection to an alternative electrical connection region 22 is made. Such is depicted in FIGS. 3a and 3b with respect to the first electrode 42.

Figure 4:
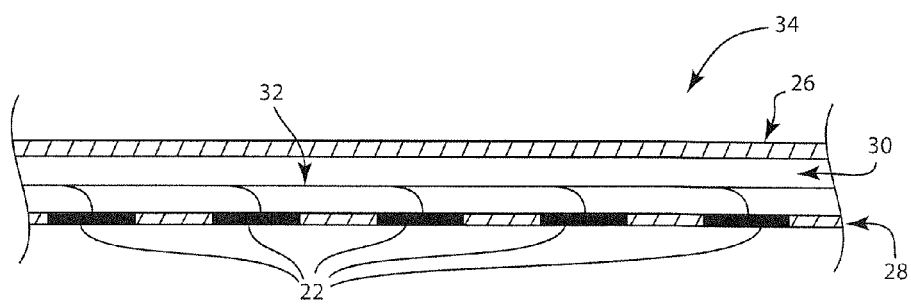
FIG. 4 depicts side view of an alternative embodiment of the conductive array.

FIG. 4 depicts a cross sectional view of an alternative embodiment of a electrode communication device 34 as taken along line 3-3 in FIG. 2. The electrode communication device 34 may comprise the first insulative layer 26 that is disposed on one side of the electrode communication device 34 and the second insulative layer 28 that is disposed on the opposite side of the electrode communication device 34. The first insulative layer 26 and the second insulative layer 28 define an internal recess 30 or space between the first insulative layer 26 and the second insulative layer 28. A single data wire 32 may connect to each of the electrical connection regions 22. The other end of the data wire 32 may connect to a data monitor (not depicted). The electrode communication device 34 utilizes the electrical connection regions 22 and the data wire 32 to transmit the collected physiological data and any signals indicative of an anatomical location from a smart electrode 10 as depicted in FIG. 1 back to the data monitor. In this embodiment, the data wire 32 may act as a data bus with all of the physiological data and the signals indicative of anatomical locations being transferred on the single data wire 32. In a similar embodiment, the data wire 32 may comprise an entire conductive sheet that extends to all of the electrical connection regions 22 of the conductive array 20.

Embodiments of the electrode communication device 34 utilizing a single conductor or data wire 32 present additional challenges as the data monitor must actively sample the physiological data from only a single electrode at a time to minimize the interference of the desired physiological data on the data wire 32 as it is transmitted to the data monitor. In such an embodiment, the data monitor may achieve this sampling through the use of a gating mechanism (not depicted) associated with the smart electrode 10 such that the smart electrode 10 only samples the physiological data upon receiving an activation signal sent out from the data monitor. If all of the smart electrodes 10 connected to the electrode communication device 34 can be sampled at a fast enough rate, the phase delay in any one of the sets of physiological data collected by a smart electrode 10 could be reduced to a clinically insignificant amount.

An advantage of an embodiment of the electrode communication device 34 comprising a single conductor or data wire 32 is that the single data wire 32 will give the conductive array 20 the most physical flexibility as it will have the fewest wires in the recess 30 that would limit the flexibility of the electrode communication device 34. A single data wire 32 of the embodiment of the electrode communication device 34 would also have the benefit of maintaining a data connection to each of the electrical connection regions 22 despite a faulty segment of the data wire as redundancy within the data wire 32 would still allow the transmission of the physiological data back to the data monitor.

Figure 5:
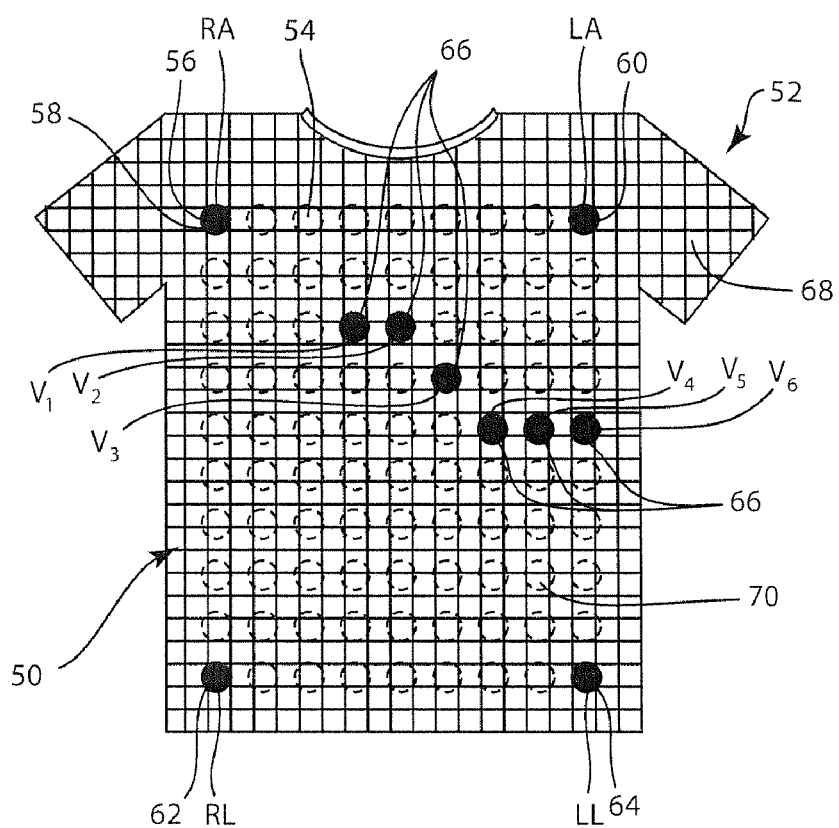
FIG. 5 depicts a further alternative embodiment of the conductive array.

FIG. 5 depicts an embodiment of the electrode communication device 50 where the electrode communication device 50 has been formed into a garment 52 such as a shirt. In the embodiment shown, the first insulative layer 26 and second insulative layer 28 depicted in FIG. 3a may comprise a material that is soft and/or comfortable to the skin of a patient such that the garment 52 is able to be worn by the patient for extended periods of time. Furthermore, the construction of the electrode communication device 50 may be such as to optimize the flexibility and malleability of the electrode communication device 50 to facilitate its use as a material in constructing a garment 52. The flexibility and/or malleability of the electrode communication device 50 may be impacted by the materials chosen for the insulative layers 26, 28 and/or the number and size of the data wires 38 as depicted in FIG. 3a. Furthermore, the flexibility and/or patient comfort may be impacted by any selections in materials for the electrical connection regions 68.

The electrode communication device 50 may comprise the entire surface area of the garment 52. In such an embodiment, any electrode 54 placed at any location on the patient's body can transmit physiological data to a data monitor (not depicted) via the electrode communication device 50. Furthermore, to facilitate the connection between any one of the electrodes 54 and the electrode communication device 50, the electrode communication device 50 may comprise a material such as nylon, lycra, or spandex to give a "compression" property to the garment 52 made of the electrode communication device 50. The "compression" quality of the garment 52 facilitates the connection between the electrodes 54 and the electrode communication device 50; however, garment 52 need not exhibit a "compression" quality to be within the scope of the present disclosure.

In an implementation using smart electrodes 56 as disclosed with respect to FIG. 1, the clinician will place the smart electrodes 56 at the specific anatomical locations as indicated on the external labels 16 of the smart electrodes 56. As an illustrative example, the smart electrodes 56 are placed at the standard anatomical locations for the collection of a typical twelve lead ECG. These anatomical locations may comprise the right arm electrode 58, the left arm electrode 60, the right leg electrode 62 and the left leg electrode 64. The smart electrode 56 may also be placed at the anatomical locations for the precordial electrodes 66 (V1, V2, V3, V4, V5, V6) or other additional precordial electrodes such as the right precordial electrodes (V4R, V5R, V6R) (not depicted) and the posterior precordial electrodes (V7, V8, V9) (not depicted). After the electrodes have been placed, the patient dons the garment 52 comprising the electrode communication device 50. The electrical connection region 68 that is aligned with one of the smart electrodes 56 forms an electrical connection with that smart electrode 56. The collected physiological data and the signal identifying the anatomical location of the electrode is transmitted to the data monitor (not depicted) for processing.

In an alternative implementation of the electrode communication device 50, the clinician may utilize standard electrodes 70 as opposed to the previously described smart electrodes 56. In this implementation, the electrode communication device 50 utilizes the plurality of data wires 38 as described in relation to FIG. 3a wherein a separate lead wire 38 is attached to each of the electrical connection regions 68 of the electrode communication device 50. The standard electrodes 70 may be placed at any position on the body of the patient. The standard electrodes 70 that are attached to the body of the patient would have to be electrodes that comprise a suitable conductive element (not depicted), such as the second conductive element 14 depicted in FIG. 1, to interface with the electrical connection regions 68 of the electrode communication device 50. The electrode communication device 50 will then use the interface between the standard electrode 70 and the electrical connection region 68 to facilitate the transfer of the physiological data collected by each of the standard electrodes 70 to the data monitor (not depicted). As a data wire (not depicted) is individually connected to each one of the electrical connection regions 68, the data monitor will be able to identify each separate signal that is obtained from an electrode 70 attached to the body of the patient. By mapping the location of each of the electrical connection regions 68, the data monitor may then extrapolate an approximate anatomical location of each of the standard electrodes 70 without receiving a signal that is indicative of the specific anatomical location, such as received from the smart electrodes 56. The functionality of the electrode communication device 50 in this implementation would therefore be similar to the functionality of other currently available electrode connection garments; however, the implementation of the electrode communication device 50 formed into a garment 52 allows for an improved electrode interface with the patient while maintaining the ability to sample the physiological data collected at each electrode and limit the tangling of the data wires.

In a still further implementation of the electrode communication device 50, a plurality of electrodes 54 are used to collect physiological data from the skin of the patient. The plurality of electrodes 54 that are attached to the skin of the patient comprise both smart electrodes 56 and standard electrodes 70. Each of the smart electrodes 56 and the standard electrodes 70 would operate in functionality as described herein. Additionally, the data monitor would be able to utilize the signals indicative of the anatomical locations of the smart electrodes 56 to create at least one reference point for the physiological data collected from the standard electrodes 70. The signals indicative of the anatomical locations of the smart electrodes 56 could be used to reference the electrical connection region 68 that is used to transmit the collected physiological data and the signal indicative of the anatomical location back to the data monitor from the smart electrode 56. Once the data monitor has a reference of an anatomical location to associate with a specific electrical connection region 68, the data monitor may extrapolate this reference out to other electrical connection regions 68 in the vicinity of the smart electrode 56 to provide a more accurate estimation of the anatomical location to which any surrounding standard electrodes 70 are attached. The combinational implementation of the smart electrodes 56 and the standard electrodes 70 would provide the clinician the ability to achieve enhanced referencing of the collected physiological data, without the added expense of requiring smart electrodes 56 for every anatomical location on the patient.

Figure 6:
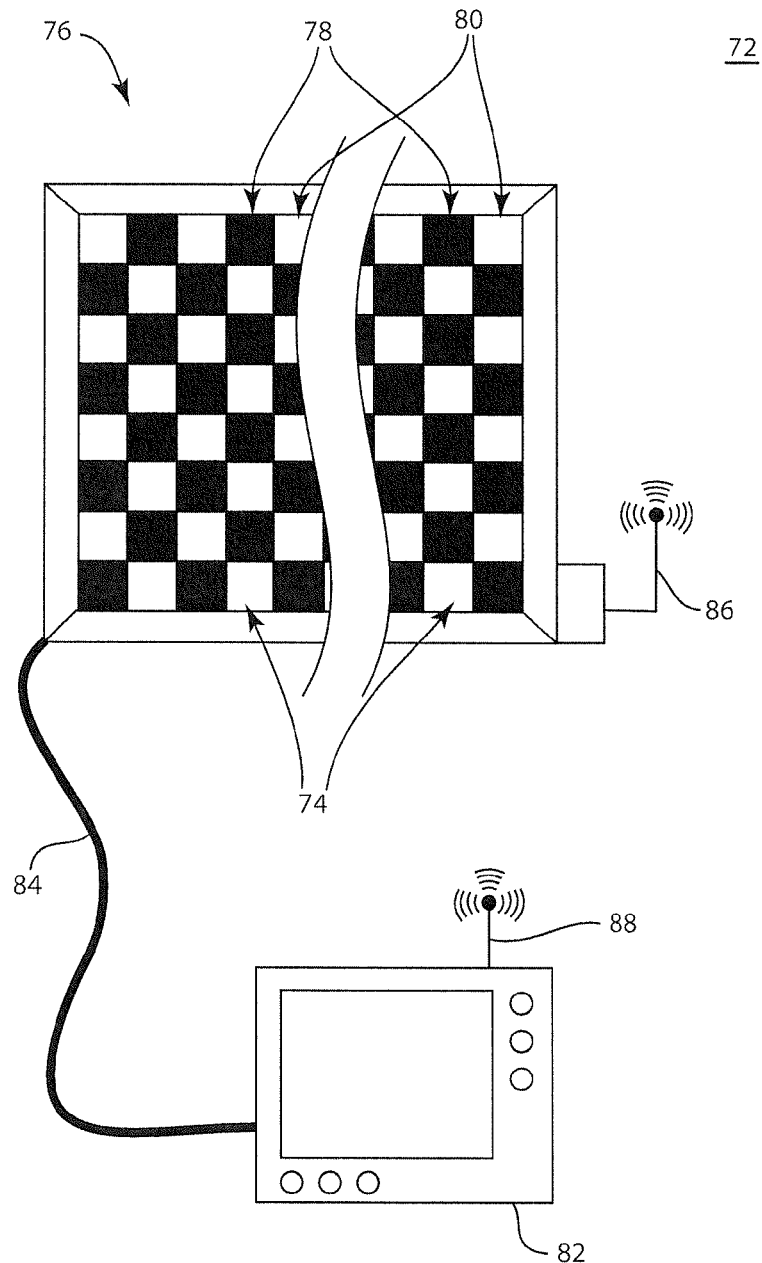
FIG. 6 depicts an embodiment of a system comprising the conductive array.

FIG. 6 depicts an embodiment of a physiological data collection system 72. In this embodiment, the electrode communication device 74 has been formed into a blanket 76 comprising a plurality of electrical connection regions 78 and a plurality of nonconductive regions 80. In the embodiment shown, the electrodes (not depicted) may be attached to the patient's body and the patient either wrapped in the blanket 76 or the patient may lie in a bed that comprises one or more blankets 76. The electrode communication device 74 of the blanket 76 provides the electrical connection regions 78 to contact the electrodes (not depicted) to facilitate the transmission of data from the electrodes to the data monitor 82. In one embodiment of the electrode communication device 74 the electrical connection regions 78 are connected by one or more data wires (not depicted) to the data monitor 82. In this embodiment, the one or more data wires may meet at a specific location of the electrode communication device 74 to form an amalgamated data cable 84 that extends from the electrode communication device 74 to the data monitor 82. The collected physiological data and any signals indicative of the anatomical location of the electrodes may be transmitted via the amalgamated data cable 84 and the electrode communication device 74 from the electrodes to the data monitor 82 where the data may be processed.

In an alterative embodiment of the electrode communication device 74, the one or more data wires (not depicted) that connect the electrical connection regions 78 to the data monitor 82 are communicatively connected to the data monitor 82 via a wireless transmitter 86 connected to the electrode communication device 74 and a wireless receiver 88 connected to the data monitor 82. In the operation of this embodiment, the physiological data and any signals indicative of the anatomical locations of the electrodes are transmitted to the wireless transmitter 86 that is connected to the electrode communication device 74. Any data or signals that are collected from the electrodes (not depicted) are transmitted via the wireless transmitter 86 to a wireless receiver 88 that is associated with the data monitor 82. The implementation of the embodiment of the conductive array 74 comprising the wireless transmitter 86 would increase the mobility of the electrode communication device 74 and further reduce any tangling and/or damage to the data wires by the elimination of the amalgamated data cable 84.

Figure 7A:
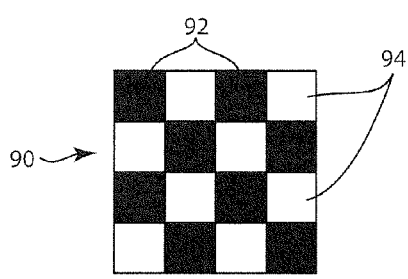
FIGS. 7a-7d depict alternative embodiments of the conductive array.

FIGS. 7a-d depict alternative embodiments of the electrode communication device 90 comprising alternative implementation of the electrical connection regions 92 and the nonconductive regions 94. FIG. 7a depicts an embodiment of the electrode communication device 90 wherein the electrical connection regions 92 are approximately the same size and shape of the nonconductive regions 94. The electrical connection regions 92 and the nonconductive regions 92 and the nonconductive regions 94 are laid out in a checked pattern which may be described as forming an electronic gingham.

Figure 7B:
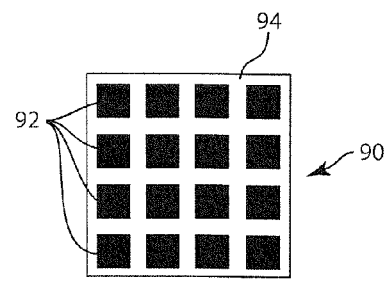

FIG. 7b depicts an embodiment of the electrode communication device 90 wherein the electrical connection regions 92 are similarly shaped to the electrical connection regions 92 depicted in FIG. 7a; however, the electrical connection regions 92 are separated by a single non-conductive region 94 that surrounds all of the electrical connection regions 92. In the embodiment of the electrode communication device 90 depicted in FIG. 7b the electrical connection regions 92 are able to be placed more closely together, thus providing greater coverage for collection of physiological signal from electrodes with the electrode communication device 90. The chance that an electrode will not achieve a suitable connection with an electrical connection region 92 is minimized by reducing the surface area of the electrode communication device 90 that is comprised by the non-conductive regions 94.

Figure 7C:
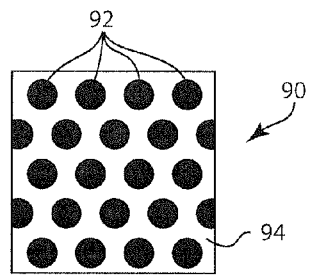

FIG. 7c depicts an embodiment of the electrode communication device 90 that is similar to the embodiment depicted in FIG. 7b, however the electrical regions 92 are in the shape of circles instead of squares. Therefore the embodiment depicted in FIG. 7c shows that the geometric shape of the electrical connection regions 92 and the nonconductive regions 94 is not herein limited to squares and may be any suitable geometrical shape as determined to facilitate the coverage of the body of the patient and/or facilitate the transmission of data from one or more electrodes attached to the patient The conductive array 90 depicted in FIG. 7c also may strike a balance between the coverage of the electrode communication device 90 that comprises electrical connection regions 92 and nonconductive regions 94. As may be determined by a visual comparison of the embodiment depicted at 7a-7c the embodiment depicted at 7c provides a larger number of electrical connection regions 92 as achieved in the embodiment depicted in FIG. 7b; however, the embodiment depicted in FIG. 7c provides a more even distribution between the percentage of the area of the conductive array 90 that is covered by electrical connection regions 92 and the area of the conductive array 90 that is covered by nonconductive regions 94.

Figure 7D:
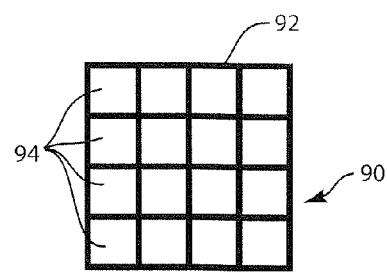

FIG. 7d further depicts an embodiment of the electrode communication device 90 wherein the electrical connection region 92 is a single region in the shape of a grid that covers the electrode communication device 90. The grid of the electrical connection region 92 is defined by a plurality of non-conductive regions 94. In the embodiment depicted in FIG. 7d the amount of area of the electrode communication device 90 that is covered by the electrical connection region may be far less than the area of the electrode communication device 90 that is covered by the non-conductive regions 94. An implementation of the embodiment depicted in FIG. 7d may comprise the use of the single data wire 32 as disclosed herein with respect to FIG. 4 as there would only be one electrical connection region 92 to which the data wire need connect.

Embodiments of the system and apparatus disclosed herein may find specific utility in the application of body surface potential mapping (BSPM). In BSPM, a plurality of electrodes are attached to the skin of the patient to obtain a more robust indication of the patient's cardiac activity. While a typical twelve lead ECG conveys much information regarding the functionality of the patient's heart, the additional channels of ECG information obtained through BSPM provide a more accurate and localized electrical picture of the depolarization of the patient's heart tissue. This improves the clinician's ability to detect scar and localized ischemic regions at a greater proficiency than using a twelve lead ECG measurement. BSPM requires a greater number of electrodes than the ten electrodes required to obtain a twelve lead ECG. Typically, BSPM can require anywhere between 20 and 128 or more electrodes collecting channels of ECG information.

One problem associated with BSPM is that the data is often hard to correlate to an anatomical location and as such the clinician is unable to identify the electrodes that coincide with the standard twelve lead ECG leads. Therefore the clinician in interpreting BSPM data is unable to utilize the standard twelve lead ECG as a reference in the interpretation. Therefore, embodiments of the system and apparatus disclosed herein may utilize the smart electrodes to collect the twelve lead ECG and standard electrode to collect the additional channels for the BSPM data. Alternatively, a smart electrode may be utilized that is indicative of the specific anatomical location of each of the electrodes for collecting the BSPM data. The additional anatomical reference data that may be monitored utilizing embodiments of the system apparatus as disclosed herein will help the clinician to more accurately and effectively interpret the BSPM data.

Furthermore, the increased number of electrodes and lead wires normally required for a BSPM procedure increases the occurrence of lead tangling and/or damage. Therefore, embodiments of the system and apparatus as disclosed herein further improve the collection of BSPM data by limiting or removing the lead wires that could become tangled or damaged during the data collection.

Another advantage of embodiments of the system and apparatus as disclosed herein is in the long term and/or overnight collection of patient physiological data. The longer the patient is connected to a data monitor for collecting physiological data the chance that the data wires may become tangled and/or damaged also increases. Therefore, by the system and apparatus disclosed herein, the instances of this tangling are further reduced allowing the patient more comfort and mobility while physiological data is being collected.

A still further advantage of embodiments of the system and apparatus disclosed herein is the ability for the clinician to dynamically change the number of electrodes from which physiological data is collected. In presently available systems and apparatus, the clinician is limited to connect only those electrodes to which there is a dedicated lead wire for that anatomical location. Furthermore, the clinician is limited in the number of electrodes that may be placed on the patient by the number of lead wires that extend out to the patient from the data monitor. Therefore, embodiments of the system and apparatus as disclosed herein allow for the clinician to attach and/or remove as many electrodes as are presently needed to collect the desired physiological data. This optimizes the efficiency of the clinician in obtaining the proper amount of physiological data for the clinician to diagnose or monitor the patient's condition.

This written description uses examples to disclose features of the embodiments, including the best mode, and also to enable any person skilled in the art to make and use the invention. The patentable scope is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

Various alternatives and embodiments are contemplated as being with in the scope of the following claims, particularly pointing out and distinctly claiming the subject matter regarded as the invention.

What is claimed is:

1. A system for obtaining physiological data from a patient and communicating the physiological data to a data monitor, comprising:
   a plurality of independently movable electrodes positionable on the patient and operable to obtain physiological data from the patient, each electrode including a first conductive element positionable in contact with the patient and a second conductive element; and
   an electrode communication device for providing a communication path from the plurality of electrodes to the data monitor, the electrode communication device having a plurality of spaced conductive regions formed along a generally planar contact surface, wherein the electrode communication device is configured to be placed over the plurality of electrodes such that the second conductive element of each electrode releasably contacts at least one of the conductive regions independent of positions of the plurality of electrodes on the patient.

2. The system of claim 1 wherein the plurality of conductive regions are spaced from each other by non-conductive regions, wherein the non-conductive regions are smaller than the second conductive element of each of the plurality of electrodes such that the second conductive element of each of the plurality of electrodes is in contact with at least one of the conductive regions when the electrode communication device is placed over the plurality of electrodes.

3. The system of claim 1 wherein the electrode communication device includes a plurality of data wires each having a first end connected to one of the conductive regions.

4. The system of claim 1 wherein the electrode communication device includes a single data wire connected to each of the conductive regions, the single data wire being configured to communicate with the data monitor.

5. The system of claim 1 wherein each of the electrodes includes electrode identifying circuitry operable to produce a signal indicative of an anatomical location on the patient to which the electrode is to be attached.

6. An apparatus for obtaining physiological data from a patient, the apparatus comprising:
   an electrode suitable to attach to the patient and collect physiological data from the patient, the electrode comprises a conductive element disposed to transmit the physiological data collected by the electrode; and
   an electrode communication device having a plurality of electrical connection regions forming a conductive array, each of the plurality of connection regions being suitable to be in electrical contact with the conductive element;
   wherein the conductive element contacts at least one electrical connection region and transmits collected physiological data to the at least one electrical connection region and upon movement by the patient or the plurality of electrical connection regions, the conductive element connects to another electrical connection region and transmits collected physiological data to the another electrical connection region.

7. The apparatus of claim 6 wherein the plurality of electrical connection regions are connected to a data monitor and the collected physiological data is transmitted through the plurality of electrical connection regions to the data monitor.

8. The apparatus of claim 7 wherein the data monitor identifies the anatomical location to which the electrode is attached.

9. The apparatus of claim 8 further comprising an electrode set comprising the electrode and the electrode comprises electrode identifying circuitry, the electrode identifying circuitry producing a signal indicative of an anatomical location on the patient to which the electrode is attached.

10. The apparatus of claim 9 wherein the data monitor uses the signal indicative of an anatomical location to identify the anatomical location to which the electrode is attached.

11. The apparatus of claim 6 further comprising at least one non-conductive region separating the plurality of electrical connection regions.

12. The apparatus of claim 11 wherein the conductive array further comprises:
   a first insulative layer disposed to a first side of the conductive array; and
   a second insulative layer covering the second side of the conductive array.

13. The apparatus of claim 12 wherein the at least one non-conductive region comprises the second insulative layer.

14. The apparatus of claim 13 further comprising a data wire disposed in a recess defined between the first insulative layer and the second insulative layer, the data wire being connected at one end to at least one of the connection regions, the other end being configured for connection to a data monitor.

15. The apparatus of claim 13 further comprising a plurality of data wires, each data wire being connected at one end to one of the connection regions of the plurality of connection regions and disposed for connection to a data monitor at the other end, the data wires being further located in a recess defined between the first insulative layer and the second insulative layer.

16. The apparatus of claim 15 where the plurality of data wires form an amalgamated data wire, the amalgamated data wire being suitable for connection to the data monitor.

17. The apparatus of claim 15 where the plurality of data wires connect to a wireless communication transmitter and the collected physiological data is wirelessly transmitted to the data monitor.

18. The apparatus of claim 13 where the first and second insulative layers comprise a material of a suitable comfort for prolonged contact with the skin of the patient.

19. A communication device to obtain physiological data from a plurality of electrodes positioned on a patient for a data monitor, each of the electrodes including a conductive element to facilitate the transmission of physiological data from the electrode, the communication device comprising:

a generally planar contact surface;

a plurality of conductive regions positioned along the contact surface, each of the conductive regions being spaced by non-conductive regions;

an insulative layer spaced from the contact surface;

at least one data wire disposed between the insulative layer and the contact surface, the at least one data wire being connected to each of the conductive regions to facilitate communication between the conductive regions and the data monitor;

wherein the conductive regions are spaced from each other such that when the communication device is positioned over the plurality of electrodes, the conductive element of each electrode is in contact with at least one of the conductive regions.

20. The communication device of claim 19 wherein the contact surface and the insulative layer are formed of a material of suitable comfort for prolonged contact with the skin of the patient.

* * * * *